US008722814B2

(12) United States Patent
Bevinakatti et al.

(10) Patent No.: US 8,722,814 B2
(45) Date of Patent: May 13, 2014

(54) METHOD OF MAKING POLYGLYCEROL ESTERS

(75) Inventors: Hanamanthsa Shankarsa Bevinakatti, Ingelby Barwick (GB); Alan Geoffrey Waite, Darlington (GB); Jackie Frank, Redcar (GB)

(73) Assignee: Croda International PLC, Goole, North Humberside (GB)

( * ) Notice: Subject to any disclaimer, the term of this patent is extended or adjusted under 35 U.S.C. 154(b) by 215 days.

(21) Appl. No.: 12/451,499

(22) PCT Filed: May 15, 2008

(86) PCT No.: PCT/GB2008/001673
§ 371 (c)(1),
(2), (4) Date: Feb. 4, 2010

(87) PCT Pub. No.: WO2008/142374
PCT Pub. Date: Nov. 27, 2008

(65) Prior Publication Data
US 2010/0144978 A1 Jun. 10, 2010

(30) Foreign Application Priority Data
May 17, 2007 (GB) .................................. 0709460.0

(51) Int. Cl.
*C08F 283/00* (2006.01)
(52) U.S. Cl.
USPC ........... 525/461; 525/410; 525/413; 525/418; 528/271; 528/370; 528/403; 554/173; 554/227
(58) Field of Classification Search
USPC .......... 525/410, 413, 418, 461; 528/271, 370, 528/403; 554/173, 227
See application file for complete search history.

(56) References Cited

U.S. PATENT DOCUMENTS

| 2,915,529 A | 12/1959 | Bell et al. |
| 3,379,693 A * | 4/1968 | Hostettler et al. ............. 525/418 |
| 5,721,305 A * | 2/1998 | Eshuis et al. .................. 524/442 |
| 5,883,274 A | 3/1999 | Shioguchi et al. |
| 6,326,459 B1 * | 12/2001 | Delaite et al. ................. 528/357 |
| 2006/0148914 A1 * | 7/2006 | Connor et al. .................. 521/48 |

FOREIGN PATENT DOCUMENTS

| EP | 1568677 | 8/2005 |
| JP | 61012603 | 1/1986 |
| WO | WO 95/21210 | 8/1995 |

OTHER PUBLICATIONS

Ai, Sakiko et al., "Effects of the Number of Fatty Acid Residues on the Phase Behaviors of Decaglycerol Fatty Acid Esters", *Journal of Colloid and Interface Science*, vol. 296, No. 2, (Apr. 15, 2006), pp. 685-689.
International Search Report dated Aug. 14, 2008 for PCT/GB/2008/001673.

* cited by examiner

*Primary Examiner* — Robert Jones, Jr.
(74) *Attorney, Agent, or Firm* — Jones Day

(57) ABSTRACT

Polyglycerol carboxylic acid esters are made by reaction of a, typically $C_2$ to $C_{30}$, particularly $C_6$ to $C_{22}$, carboxylic acid with glycerol carbonate, particularly with base catalyst, and desirably at temperatures from 170° C. to 250° C. Other carbonates e.g. cyclic diol carbonates such as ethylene or propylene carbonates, may be used in combination with the glycerol carbonate to make novel mixed polymeric esters. The molar ratio of carboxylic acid group to glycerol carbonate is typically from 2 to 30, but can be up to 100. The base catalyst is desirably alkali metal hydroxide, carbonate or alkoxide. The reaction is desirably carried out in an inert atmosphere, and reducing agent such as phosphorous acid, hypophosphorous acid or borohydride and/or activated carbon, may be included to improve product color.

24 Claims, No Drawings

METHOD OF MAKING POLYGLYCEROL ESTERS

CROSS REFERENCE TO RELATED APPLICATION

This application is the National Phase application of International Application No. PCT/GB2008/001673, filed 15 May 2008, which designates the United States and was published in English. The related application, in its entirety, is incorporated herein by reference.

This invention relates to the manufacture of carboxylic acid esters of polyglycerol, particularly esters with relatively long chain fatty acids.

Polyglycerol fatty acid esters are known materials and have been made and used as surfactants, particularly emulsifiers e.g. in food and personal care products, for many years. Patents on their manufacture were filed in the 1930s e.g. U.S. Pat. No. 2,182,397, and they have been in use since the 1940s in Europe and America, being approved for food use in the USA in the 1960s. They are recognised as having a good toxicology and safety profile. Conventionally, they are made by the reaction of fatty acids or, usually lower alkyl, esters with polyglycerols typically under base catalysis in esterification or transesterification reactions.

Glycerol/glycerine carbonate (4-hydroxymethyl-1,3-dioxolan-2-one) has been known as a compound for many years. It has become commercially available from routes including reacting glycerol with phosgene or an alkylene) carbonate, see U.S. Pat. No. 2,915,529 or JP 63-029663 A, catalytic reaction of glycerol, carbon monoxide and oxygen, see U.S. Pat. No. 5,359,094, or reacting urea with dialkyl carbonates; see U.S. Pat. No. 6,025,504 or U.S. Pat. No. 6,495,703. Prior described reactions with glycerol carbonate generally utilise reagents which are miscible with glycerol carbonate e.g. glycerol to make polyglycerol—see U.S. Pat. No. 5,721,305, U.S. Pat. No. 5,723,696, JP 10-072392 A and JP 10-072393 A, or other short chain polyols such as trimethylol propane to make hyperbranched polyethers—see G. Rokicki et al, Green Chemistry, 2005, 7, 529.

This invention is based on our discovery that polyglycerol esters can be made by building the polyglycerol chain onto a carboxylic, particularly a fatty carboxylic, acid starting group using glycerol carbonate, even though many carboxylic acids, particularly relatively long chain ("fatty") acids, are not miscible with glycerol carbonate.

The present invention accordingly provides a method of making a polyglycerol carboxylic acid ester in which a carboxylic acid, particularly a fatty carboxylic acid, is reacted with glycerol carbonate.

Where the carboxylic acid and glycerol carbonate are immiscible, at the start of the reaction, the reactants form a two phase liquid system. As the (poly)glycerol chain of the esters grows, the esters become increasingly miscible with the glycerol carbonate. Thus, the product esters and to an extent the intermediate esters will tend to act to compatibilise the starting materials, but when the transition to a single phase system occurs will depend on the reagents used. Reaction between components (generally) in different phases will be slower than when they are in one phase. Also reaction between the carboxylic acids (as carboxylate, see the discussion on catalysis below) and the glycerol carbonate is kinetically favoured as compared with reaction between an intermediate carboxylic acid (poly)glycerol ester and further glycerol carbonate. The degree of compatibility of the intermediate esters may influence the relative speed of reaction as against chain length and thus influence the spread of chain lengths in the final product. If desired, the physical immiscibility of the starting materials may be avoided by the use of suitable solvent(s) (see below).

The reaction proceeds slowly unless a catalyst, particularly a base catalyst, is used, and the invention accordingly includes a method of making a polyglycerol carboxylic acid ester in which a carboxylic acid is reacted with glycerol carbonate, in the presence of a base catalyst. Without being bound by any particular explanation, we believe the catalyst reacts with the acid to form a carboxylate ion which reacts with the carbonate by a nucleophilic reaction, displacing the carbonate at the 1- or 2-position in the glycerol, with subsequent decarboxylation with evolution of $CO_2$. This initial reaction seems to be kinetically faster than subsequent chain extension reaction steps which appear to involve base reacting with free OH on the intermediate ester to form alkoxide which reacts further with carbonate analogously. Suitable catalysts include alkali metal, particularly sodium or potassium, bases e.g. hydroxides, particularly NaOH or KOH, carbonates, particularly $K_2CO_3$ or $Na_2CO_3$, bicarbonates, particularly $KHCO_3$ or $NaHCO_3$ and alkoxides particularly sodium or potassium lower, particularly $C_1$ to $C_4$, alkoxides e.g. sodium or potassium methoxide, and tertiary amines, particularly tertiary amines including at least one tertiary nitrogen atom in a ring system, such as 1,8-diazabicyclo[5.4.0]undec-7-ene (DBU), 1,4-diazabicyclo[2.2.2]octane (DABCO), 4-(dimethylamino)pyridine (DMAP), 7-methyl-1.5.7-triazabicyclo[4.4.0]dec-5-ene (MTBD), quinuclidine, pyrrocoline and similar materials. Base catalyst, particularly alkali metal hydroxide may be partially neutralised (or buffered) with acid, particularly fatty acid used in the esterification reaction—in effect using a fatty acid soap as catalyst—or a polybasic acid such as phosphorus oxyacid e.g. phosphoric acid, or (see also below) reducing phosphorus oxyacids such as phosphorous acid, (in a way similar to catalyst used to make sorbitan esters).

The amount of catalyst used will typically be from 0.5 to 25, more usually 2 to 20, and particularly 5 to 15, mol %, based on the carboxylic acid starting material. Potassium carbonate, desirably used in an amount of from 3 to 18, especially from 5 to 12 mol % based on the carboxylic acid starting material, is a particularly useful catalyst.

Particularly when catalysed, we have found that the reaction proceeds readily to completion i.e. complete consumption of the glycerol carbonate. This gives rise to a practical benefit of the invention that the molar ratio of acid starting group to glycerol carbonate used generally determines the (average) length of the polyglycerol chain (but see below on side reactions). Using the carboxylic acid as the chain starter also means that the reaction produces mono-esters as the main product, generally without significant quantities of bis-carboxylic acid or higher esters. (Theoretically small amounts may be made by transesterification reactions but we have not seen such compounds in products made by the method of this invention.)

The carboxylic acid used as the starting group in this method will generally be a $C_2$ to $C_{30}$, typically a $C_6$ to $C_{22}$ carboxylic acid. As the esters will commonly be used as surfactants the acid will more generally be a $C_8$ to $C_{22}$, typically $C_{10}$ to $C_{22}$, and particularly $C_{12}$ to $C_{18}$, monocarboxylic acid. The carboxylic acid may be linear or branched, saturated or unsaturated, and suitable examples include lauric, myristic, palmitic, palmitoleic, stearic, iso-stearic (a mixture of mainly branched adds with a range of chain lengths averaging about $C_{18}$), oleic, linoleic, linolenic, behenic, erucic or omega 3-, 6- or 9-fatty, acids. Mixtures of carboxylic adds may be used if desired.

In addition to glycerol carbonate, other cyclic carbonates e.g. ethylene glycol, propylene glycol and/or propylene1,3-diol (trimethylene) carbonates may be included, with the effect of adding the corresponding dial units into the polymeric chain—ethyleneoxy and 1,2-propyleneoxy units being familiar to surfactant chemists from polymerisation of the corresponding alkylene oxides. Such inclusions will modify chain properties somewhat, in particular with 1,2- and 1,3-propyleneoxy units tending to make the chains less hydrophilic. The proportion of such other carbonates used will typically be less than 75, more usually less than 50 and generally less than 25, mole % of the total carbonate used in the synthesis. The invention further includes a method of making a mixed poly(alkyleneoxy)/polyglycerol carboxylic acid ester in which a carboxylic add is reacted with glycerol carbonate and at least one other cyclic carbonate, particularly in the presence of a base catalyst. The mixed ester can be a block or random (statistical) copolymeric ester, and the product can readily be determined by controlling how the carbonate reagents are supplied to the reaction. Block copolymers can be made by substantially completing reaction with one carbonate before the (an)other is added. Statistical copolymers can be made by supplying a mixture of carbonate reagents to the reaction. Taper block copolymers can be made by adding the (an)other carbonate reagent later than but before complete reaction of a first carbonate reagent. Sequential block, block random and similar types of copolymeric chains can be made by combinations or ready variations on the above reaction sequences.

The copolymeric types of esters made by these reactions are believed to be novel compounds and the invention accordingly includes a mixed poly(alkyleneoxy)/polyglycerol ester of a carboxylic acid, particularly a fatty, especially a C8 to C22, carboxylic acid.

In particular the mixed esters are of the formula:

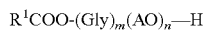

where
$R^1$ is a C1 to C21 hydrocarbyl, particularly alkyl, alkenyl or alkadienyl, group;
Gly is a glyceryl residue and
AO is an alkyleneoxy residue of a corresponding diol cyclic carbonate, in any order;
m is from 1 to 100; and n is from 1 to 75; typically such that n+m is from 2 to about 100.

Typically the average degree of polymerisation (DP) i.e. the chain length, of the polyglycerol chain(s) will be in the range from 2 to about 100, particularly from 2 to 50, though more usually the chain lengths will correspond to those of typical commercially available polyglycerols e.g. 2 to 30 and more usually from 2 to 20, particularly 2 to 10. Although the synthetic reaction appears robust enough to make products with chain lengths above about 30, reaction rates may fall off somewhat at higher chain lengths, which could be balanced by top up (or continuous) addition of glycerol carbonate and/or catalyst, and side reactions may give rise to lower product purity (see below). Accordingly, the molar ratio of carboxylic acid group to glycerol carbonate used in the method is generally from 1:2 to 1:100, typically 1:2 to 1:50, though more usually from 1:2 to 1:30, desirably 1:2 to 1:25 and particularly from 1:2 to 1:20.

The product of the reaction is a mixture of (poly)glycerol esters having a range of DP (chain length). In principle, particularly where the average DP is relatively low e.g. 5 or below, the chain may include DP 1 materials i.e. carboxylic acid monoglycerol esters (otherwise known as carboxylic acid monoglycerides). In this respect, the products of the present method differ from conventional polyglycerol esters because in commercial polyglycerol, residual free glycerol is generally removed by distillation. Additionally, the products of this reaction normally contain substantially no polyglycerol bis-carboxylic acid ester, because the reaction between carboxylic acid (carboxylate) and glycerol carbonate is faster than the subsequent chain extension. In addition to the (poly)glycerol esters the reaction may generate (poly)glycerol in side reactions such as reaction of glycerol carbonate with free water (see below) or free glycerol, or by polymerisation of glycerol carbonate onto the free OH group of glycerol carbonate. Generally, the more glycerol carbonate (as such) present in the reaction system the more likely polyglycerol is to be made.

It may be desirable to include reducing agent in the reaction to aid in colour control, particularly as thermal exposure of carboxylic acids, especially unsaturated fatty acids, may give rise to more highly coloured products. Reducing agents commonly used for this purpose, particularly in the manufacture of food or personal care products can be used in this invention and examples include phosphorous acid ($H_3PO_3$), hypophosphorous acid ($H_2PO_3$) and borohydride (usually as sodium borohydride). Where the reducing agent is itself an acid e.g. phosphorous or hypophosphorous acid, it will usually be present as a salt, typically an alkali metal salt. The salt may be made in situ by reaction with base e.g. part of the basic catalyst (where used) and in this case care may be needed to ensure that sufficient base is present to neutralise the reducing acid and to act as catalyst. When used the amount of reducing agent will typically be from 0.1 to 15%, more usually 1 to 10%, and particularly 2 to 7.5%, by mole based on the carboxylic acid groups in the starting material.

Another way of reducing product colour is to include particulate carbon, particularly so-called "activated carbon", in the reaction to absorb coloured side products. When used, the amount of carbon will typically be from 0.5 to 2.5 weight % of the total reagents. Of course, this carbon will generally be removed e.g. by filtration, before the products are included in end use formulations. Activated carbon and a reducing agent may be used together in the reaction if desired.

Further colour improvement can be achieved by treatment of the reaction product with particulate carbon, particularly activated carbon, typically at from 0.5 to 2.5 weight % of the product, or by bleaching the product of the reaction e.g. with a peroxide based bleach, generally after removal of any activated carbon.

Typically the reaction temperature will be superambient, typically at least 100° C. and more usually at least 150° C. Using alkali metal base catalysis, the reaction may be very slow at temperatures below about 170° C. and desirably the reaction temperature is at least 175° C., more usually at least 180° C. The reaction temperature may be as high as 250° C., though, generally the desire to avoid undue coloration in the product will give a preference for somewhat lower temperatures, with the range 180 to 220° C. being generally suitable. We have found that it is usually desirable to use somewhat higher reaction temperatures with relatively longer chain carboxylic acids to counteract the trend towards reduced compatibility of the acid with the glycerol carbonate. Such reduced compatibility would otherwise tend to lead to possible phase separation and, by thus slowing the desired reaction, increased production of polyglycerol by-product. Thus for relatively shorter chain fatty acids e.g. lauric acid, desirable reaction temperatures are from 180 to 200° C., particularly 180 to 190° C., for the relatively longer chain palmitic and stearic acids, desirable reaction temperatures are from 190 to 220° C., particularly 200 to 220° C.

The reaction and its completion can conveniently be monitored using standard IR e.g. FT-IR, and HPLC techniques. Under the conditions set out above the reaction generally runs to completion (monitored as described above) so that the reaction mixture is the polyglycerol ester product together with catalyst residues and, generally low levels of, impurities (other than polyglycerol—see discussion above). We have seen reaction times typically in the range 1 to 20 hours with most being complete in from 1.5 to 15 hours, usually from 2 to 14 hours. When the cyclic carbonate is added periodically or gradually during the reaction it will usually be desirable to maintain the reaction temperature for a period e.g. an hour or two, after the last addition to ensure complete reaction.

We have found that the reaction can be carried out without the need for a solvent or diluent and we expect that this is how the reaction will be carried out generally, particularly as this will avoid any problem in isolating the desired product. However a suitable inert reaction medium, solvent or diluent may be used if desired. Suitable such materials are liquids which remain thermally stable and are inert to the reagents and products. Any solvent used will either have a relatively low vapour pressure at the reaction temperature or the reaction will be conducted under suitable containment or reflux arrangements. Suitable examples of solvents or diluents include dimethyl isosorbide (BP 118 to 120° C. at 20 mbar), dimethytformamide (BP 153° C.), dimethylsulfoxide (BP 189° C.), ethylene glycol and diethylene glycol diethers e.g. dimethyl, diethyl or dibutyl ethers.

Solvent and/or diluent may be included with the product, either by leaving reaction solvent/diluent in the product or by subsequent addition, to reduce product viscosity for transport, storage and/or subsequent use. Suitable solvents/diluents for this purpose include those mentioned above as well as glycerol carbonate (when its reactivity does not interfere with downstream product use), glycerol or, and particularly, monopropylene glycol because this may give the additional benefit of improving the molecular packing of the polyglycerol ester at the phase interface in end use formulations. Typically such solvents/diluents will be used in amounts to give formulations having from 50 to 90, more usually 60 to 80 and particularly about 70,% by weight of polyglycerol ester.

Typically the reagents used in the method remain liquids of low vapour pressure at reaction temperatures so the reaction can be conveniently carried out at ambient pressure though moderately superambient pressure may be used if desired. We think it unlikely that it will be desirable to use subambient pressure but by choosing suitable involatile reagents it may be possible to carry the reaction out at moderately subambient pressure.

To help avoid excessive colour generation, particularly when reacting unsaturated acids, the reaction will usually be carried out in a largely oxygen free atmosphere, e.g. In a nitrogen atmosphere. In laboratory scale synthesis, this has not needed to be more elaborate than using a nitrogen blanket or sparge. Larger scale manufacture may be less sensitive because of the relatively lower exposed surface area generally possible in such larger scale synthesis.

The cyclic carbonate reagent(s) used in this invention may react with free water in the reaction mixture forming polyglycerol. This is generally not preferred, and it is accordingly desirable to use dry reagents—if necessary removing water from the reagents used, most notably, the fatty acid. Suitably, fatty acid drying may be done by heating to evaporate the water e.g. under vacuum, before mixing the cyclic carbonate reagent with the fatty acid. The base catalyst may react with the fatty acid to form a salt (soap) and small amounts of water so such evaporative drying may be carried out after combining the base catalyst and the fatty acid. For corresponding reasons, it also is desirable to use cyclic carbonates which have a low content of free polyol such as glycerol.

Generally we expect that the reaction will be carried out in a batch mode, typically by mixing the reagents in a suitable vessel and allowing them to react, usually under stirring for a suitable time (see above). As noted above fresh reagent, particularly glycerol carbonate, and/or catalyst may be added occasionally, at multiple intervals or continuously during the reaction (semi-batch operation). It is also possible to use continuous or semi-continuous reaction modes if desired.

Polyglycerol esters can be used in a wide variety of applications. In food and/or cosmetic applications and products, they are typically used as oil in water and sometimes as water in oil emulsifiers, solubilizers, emollients, dispersants, spreading agents and rheology modifiers. In industrial applications, they are used as oil in water and sometimes as water in oil emulsifiers, dispersants, and potentially in antifog, antistatic, lubrication or plasticizer applications.

The following Examples illustrate the invention. All parts and percentages are by weight unless otherwise stated.

Materials

Fatty acids (Abbreviated FA)
    FA1 octanoic acid, ex Uniqema (Croda)
    FA2 lauric acid, Prifrac 2920 ex Uniqema (Croda)
    FA3 coconut oil fatty acid (COFA), ex Uniqema (Croda)
    FA4 palmitic acid, ex Uniqema (Croda)
    FA5 stearic acid, ex Uniqema (Croda)
    FA6 iso stearic acid, ex Uniqema (Croda)
    FA7 oleic acid Catalysts
    Cat1 NaOH
    Cat2 K2CO3
    Cat3 Na2CO3
    Cat4 KOH
    Cat5 1,8-diazabicyclo[5.4.0]undec-7-ene (DBU)

Oils
    Oil1 hexadecane Arlamol HD ex Uniqema (Croda)

Test Methods

The stability of the emulsions was assessed by making up water in oil emulsions as described below. 100 g of formulation was made by dissolving 1 g of test product in 79 g distilled water and heating to 75° C. in a water bath. 20 g of Oil1 was separately heated to 75° C. on a water bath and at 75° C., the oil phase was added to the water phase under stirring with an overhead driven propeller blade stirrer [500 rpm (ca 8 Hz)] and then homogenised with an Ultra Turrax [12000 rpm (200 Hz)] for 2 minutes. The emulsion was then allowed to cool to ambient temperature under stirring [overhead stirrer at 300 rpm (5 Hz)]. Emulsions were stored at ambient temperature and at 50° C. and their stability visually assessed at intervals of 1 day (1 d), 1 week (1 w) and 1 month (1 m). The emulsions were rated as: NS=No Separation; TTO=Trace of oil separation at the top of emulsion; x % STO=percent oil separation at top of emulsion; Br=Emulsion broken.

SYNTHESIS EXAMPLES

Synthesis Example

SE1

Lauric acid (10.8 g; 0.05 mol), glycerol carbonate (29.5 g; 0.25 mol) and sodium hydroxide (0.10 g 5 mol % based on lauric acid), were charged to a 100 ml round bottomed flask fitted with magnetic stirrer bar, nitrogen sparge, side-arm water condenser and collection flask. The mixture was heated under stirring and gentle nitrogen sparge on an oil bath, itself heated with a hotplate with stirrer motor until the oil temperature was 180° C. The reaction mixture was then maintained at an oil bath temperature of 180° C., until all of the glycerol carbonate had been consumed, as monitored by FT-IR and HPLC. The reaction was then stopped and the product discharged.

Synthesis Examples

SE2 to SE23

Further polyglycerol fatty acid polyesters were made by the general method set out in Synthesis Example SE1 making appropriate changes to the materials, proportions or conditions. The reactions were monitored and the identity of the products was confirmed using IR spectroscopy and HPLC.

The materials used, reaction conditions and products are summarised in Table SE1 below.

TABLE SE1

| Ex No | FA | Ratio[1] | Catalyst type | mol %[2] | Reaction Conditions[3] | Product |
|---|---|---|---|---|---|---|
| SE1 | FA1 | 1:5 | Cat2 | 5 | 1/170 + 7/180 | pentaglycerol octanoate |
| SE2 | FA3 | 1:2 | Cat2 | 2 | 3/170 + 4/180 | diglycerol cocoate |
| SE3 | FA2 | 1:4 | Cat1 | 5 | 6/180 | tetraglycerol laurate |
| SE4 | FA2 | 1:5 | Cat1 | 5 | 5/180 | pentaglycerol laurate |
| SE5 | FA2 | 1:5 | Cat1[4] | 5 | 5/180 | pentaglycerol laurate |
| SE6 | FA2 | 1:5 | Cat2[5] | 4 | 3/180 + 6/190 | pentaglycerol laurate |
| SE7 | FA2 | 1:5 | Cat3[4] | 5 | 4/180 | pentaglycerol laurate |
| SE8 | FA7 | 1:5 | Cat2 | 5 | 1.5/213 | pentaglycerol oleate |
| SE9 | FA2 | 1:10 | Cat1 | 5 | 12/180 + 2/190 | decaglycerol laurate |
| SE10 | FA4 | 1:5 | Cat2 | 5 | 4.5/180 | pentaglycerol palmitate |
| SE11 | FA4 | 1:10 | Cat2 | 5 | 8/200 | decaglycerol palmitate |
| SE12 | FA5 | 1:5 | Cat1 | 5 | 5/220 | pentaglycerol stearate |
| SE13 | FA6 | 1:5 | Cat1 | 5 | 5/200 | pentaglycerol iso-stearate |
| SE14 | FA2 | 1:5 | Cat1 | 1 | 8/190 | pentaglycerol laurate |
| SE15 | FA2 | 1:5 | Cat4 | 1.4 | 9.5/190 | pentaglycerol laurate |
| SE16 | FA2 | 1:5 | Cat1 | 2 | 9.5 190 | pentaglycerol laurate |
| SE17 | FA6 | 1:10 | Cat1 | 5 | 4/210 | decaglycerol laurate |
| SE18 | FA2 | 1:20 | Cat1 | 5 | 9/190 | polyglycerol-20 laurate |
| SE19 | FA2 | 1:50 | Cat1 | 5 | 14/190 | polyglycerol-50 laurate |
| SE20 | FA2 | 1:5 | Cat5 | 5 | 2/190 | pentaglycerol laurate |
| SE21 | FA5 | 1:10 | Cat2 | 10 | 1.5/216 | decaglycerol stearate |
| SE22 | FA5 | 1:20 | Cat2 | 10 | 1.5/216 | decaglycerol stearate |
| SE23[6] | FA6 | 1:10 | Cat1 | 5 | 2/210 | pentaglycerol iso-stearate |
| SE24 | FA7 | 1:15 | Cat2 | 10 | 1/217 | polyglycerol-15 oleate |
| SE25 | FA7 | 1:20 | Cat2 | 10 | 1.5/212 | polyglycerol-20 oleate |

[1]molar ratio fatty acid:glycerol carbonate
[2]mol % of catalyst based on fatty acid
[3]time (hours)/oil bath temperature (° C.)
[4]catalyst pre-reacted with fatty acid to form a mixture of fatty acid and fatty acid soap
[5]1.7 mol % (on fatty acid) of $H_3PO_3$ was added with the catalyst
[6]15 g dimethyl isosorbide was used as solvent with iso-stearic acid (7.1 g: 0.025 mol) and glycerol carbonate (29.5 g; 0.25 mol).

Synthesis Examples

SE26 and 27

In these, a combination of ethylene carbonate and glycerol carbonate were used to produce mixed eaters i.e. poly(glycerol) poly(ethyteneoxy) esters. The reactions were carried out as described in
Synthesis Example SE1 except that the reaction with ethylene carbonate was completed before the glycerol carbonate was added.

The materials used, reaction conditions and products are summarised in Table SE 2 below.

TABLE SE2

| Ex No | FA | Ratio[1] | Catalyst type | mol %[2] | Reaction Conditions[3] | Product |
|---|---|---|---|---|---|---|
| SE26 | FA7 | 1:5:10 | Cat2 | 5 | [4/200 + 1/217] 1/217 | 10G-15EO oleate |
| SE27 | FA6 | 1:5:10 | Cat2 | 5 | [3/200 + 2/216] 1/216 | 10G-15EO iso-stearate |

[1]the molar ratio is fatty acid:ethylene carbonate:glycerol carbonate
[2]mol % of catalyst based on fatty acid
[3]reaction conditions are given as described in Table SE1 with those for the reaction with ethylene carbonate in square brackets [ ]

Application Examples

Some of the polyglycerol esters made in Synthesis Examples SE1 to SE17 were screened for their ability to stabilise water in oil emulsions as described above. The results are set out in Table AE1 below.

TABLE AE1

| Ex No | SE No | Ambient Temperature | | | 50° C. | | |
|---|---|---|---|---|---|---|---|
| | | 1 d | 1 w | 1 m | 1 d | 1 w | 1 m |
| AE1.1 | SE1 | NS | NS | TTO | TTO | Br | Br |
| AE1.2 | SE2 | NS | NS | NS | TTO | 5% STO | 5% STO |
| AE1.3 | SE3 | NS | NS | NS | TTO | TTO | 5% STO |
| AE1.4 | SE4 | NS | NS | NS | NS | TTO | TTO |
| AE1.5 | SE5 | NS | NS | NS | NS | TTO | TTO |
| AE1.6 | SE6 | NS | NS | NS | NS | TTO | 5% STO |
| AE1.7 | SE7 | NS | NS | NS | TTO | TTO | TTO |
| AE1.9 | SE9 | NS | NS | NS | NS | NS | TTO |
| AE1.10 | SE10 | NS | NS | NS | NS | TTO | TTO |
| AE1.11 | SE11 | TTO | TTO | NS | TTO | TTO | TTO |
| AE1.12 | SE12 | NS | NS | TTO | NS | TTO | 5% STO |
| AE1.13 | SE13 | NS | NS | NS | NS | TTO | 5% STO |
| AE1.14 | SE14 | NS | NS | — | TTO | Br | — |
| AE1.15 | SE15 | NS | NS | — | NS | 5% STO | — |
| AE1.16 | SE16 | NS | NS | — | NS | 5% STO | — |
| AE1.18 | SE18 | NS | NS | — | NS | NS | — |
| AE1.19 | SE19 | NS | NS | — | NS | NS | — |

The invention claimed is:

1. A method of making a polyglycerol carboxylic acid ester, comprising reacting a carboxylic acid with glycerol carbonate; wherein the resulting polyglycerol carboxylic acid ester has a molar ratio of carboxylic acid residue to glycerol residues from the glycerol carbonate in the range of 1:2 to 1:100.

2. A method of making mixed poly(alkyleneoxy)/polyglycerol carboxylic acid ester, comprising reacting a carboxylic acid with glycerol carbonate and at least one other cyclic carbonate; wherein the resulting polyglycerol carboxylic acid ester has a molar ratio of carboxylic acid residue to glycerol residues from the glycerol carbonate in the range of 1:2 to 1:100.

3. A method as claimed in claim 2 wherein the other cyclic carbonate is ethylene glycol carbonate, propylene glycol carbonate and/or propylene1,3-diol (trimethylene) carbonate.

4. A method as claimed in claim 1 wherein the carboxylic acid is or includes at least one $C_2$ to $C_{30}$ fatty acid.

5. A method as claimed in claim 4 wherein the carboxylic acid is a $C_6$ to $C_{22}$.

6. A method as claimed in claim 1 wherein the reaction mixture includes a catalyst.

7. A method as claimed in claim 6 wherein the catalyst is a basic catalyst.

8. A method as claimed in claim 7 wherein the catalyst is at least one alkali metal hydroxide, carbonate or alkoxide and/or at least one tertiary amine.

9. A method as claimed in claim 6 wherein the amount of catalyst is from 0.5 to 25%.

10. A method as claimed in claim 1 wherein the reaction mixture further includes a reducing agent and/or activated carbon and/or the reaction product is treated with activated carbon and/or a bleaching agent.

11. A method as claimed in claim 10 wherein the reducing agent is at least one of phosphorous acid, hypophosphorous acid and borohydride.

12. A method as claimed in claim 10 wherein the amount of reducing agent is from 0.1 to 15%.

13. A method as claimed in claim 1 wherein the reaction temperature is from 170° C. to 250° C.

14. A method as claimed in claim 1 wherein the reaction is carried out in an inert atmosphere.

15. A method as claimed in claim 1 wherein the reaction is carried out in an inert solvent or diluent.

16. A mixed poly(alkyleneoxy)/polyglycerol ester of a carboxylic acid.

17. The mixed ester of claim 16, wherein the mixed ester comprises the formula:

$$R^1COO\text{-}(Gly)_m(AO)_n\text{---}H$$

wherein:
R$^1$ represents a $C_1$ to $C_{21}$ hydrocarbyl group;
Gly represents a glyceryl residue;
AO represents an alkyleneoxy residue of a corresponding diol cyclic carbonate, in any order;
m is from 1 to 100; and
n is from 1 to 75.

18. The mixed ester of claim 17, wherein the alkyleneoxy groups are ethyleneoxy, 1,2-propyleneoxy or 1,3-propyleneoxy groups.

19. A mixed ester as claimed in claim 16 which is a block or random (statistical) copolymeric ester.

20. The mixed ester of claim 17, wherein the hydrocarbyl is an alkyl, an alkenyl, or an alkadienyl group.

21. A composition, comprising a poly(alkyleneoxy)/polyglycerol ester of a carboxylic acid; wherein the ester has a molar ratio of carboxylic acid residue to glycerol residues from the glycerol carbonate in the range of 1:2 to 1:100.

22. The composition of claim 21, wherein the composition comprises a poly(alkyleneoxy)/polyglycerol ester of the formula:

$$R^1COO\text{-}(Gly)_m(AO)_n\text{---}H$$

wherein:
R$^1$ represents a $C_1$ to $C_{21}$ hydrocarbyl;
Gly represents a glyceryl residue;
AO represents an alkyleneoxy residue of a corresponding diol cyclic carbonate, in any order;
m is from 1 to 100; and
n is from 1 to 75.

23. A mixed poly(alkyleneoxy)/polyglycerol carboxylic acid ester, wherein the mixed poly(alkyleneoxy)/polyglycerol carboxylic acid ester is prepared according to the method of claim 2.

24. A composition comprising a mixed poly(alkyleneoxy)/polyglycerol carboxylic acid ester, wherein the mixed poly(alkyleneoxy)/polyglycerol carboxylic acid ester is prepared according to the method of claim 2.

* * * * *